United States Patent [19]

Roger, Jr. et al.

[11] Patent Number: 5,324,504

[45] Date of Patent: Jun. 28, 1994

[54] PERFLUORO-T-BUTYL-CONTAINING COMPOUNDS FOR USE IN FLUORINE-19 NMR AND/OR MRI

[75] Inventors: Walter J. Roger, Jr., Ellicott City; Thomas S. Everett, Lutherville, both of Md.

[73] Assignees: The Johns Hopkins University, Baltimore; Towson State University, Lutherville, both of Md.

[21] Appl. No.: 10,013

[22] Filed: Mar. 4, 1993

Related U.S. Application Data

[62] Division of Ser. No. 762,445, Sep. 19, 1991, Pat. No. 5,234,680, which is a division of Ser. No. 388,049, Jul. 31, 1989, Pat. No. 5,116,599.

[51] Int. Cl.$^5$ .............. A61B 5/055; C07C 53/21; C07C 211/03; A61K 31/20
[52] U.S. Cl. .............. 424/9; 554/226; 562/553; 562/574; 514/558; 514/561; 514/832; 436/173; 436/806; 128/653.4
[58] Field of Search .............. 424/9; 554/226; 562/553, 574; 514/832, 558, 561; 436/173, 806; 128/653.4, 654

[56] References Cited

U.S. PATENT DOCUMENTS

| | | |
|---|---|---|
| 3,911,138 | 10/1975 | Clark, Jr. .............. 514/746 |
| 4,105,798 | 8/1978 | Moore et al. .............. 514/756 |
| 4,284,558 | 9/1981 | Barton et al. .............. 540/25 |
| 4,325,972 | 4/1982 | Geyer et al. .............. 514/579 |
| 4,523,039 | 6/1985 | Lagow et al. .............. 568/615 |
| 4,558,279 | 12/1985 | Ackerman et al. .............. 424/315 |
| 4,612,185 | 9/1986 | Dean .............. 424/9 |
| 4,640,833 | 2/1987 | Tamborski et al. .............. 424/5 |
| 4,775,522 | 10/1988 | Clark .............. 424/9 |
| 4,820,505 | 4/1989 | Ginsberg et al. .............. 424/9 |
| 4,865,836 | 9/1989 | Long, Jr. .............. 424/5 |

FOREIGN PATENT DOCUMENTS 0118281 9/1984 European Pat. Off. .

OTHER PUBLICATIONS

Whitmore, Organic Chemistry, D. Van Nostrand Company, Inc., N.Y., N.Y. (C) 1937, pp. 548–579 (Carbohydrates, Glucocides, Saccharides) 520–547 not provided.
Morrison & Boyd, Organic Chemistry (2nd Ed.), Allyn & Bacon, Inc., (C) 1966, pp. 708–709.
D. Eidelberg et al., "$^{19}$F NMR Imaging of Blood Oxygenation in the Brain," Magnetic Resonance in Medicine, vol. 6, pp. 344–352 (1988).
(List continued on next page.)

Primary Examiner—Gary E. Hollinden
Attorney, Agent, or Firm—Banner, Birch, McKie and Beckett

[57] ABSTRACT

Accordingly, the present invention is directed to biological compounds derivatized so as to contain at least one perfluoro-t-butyl moiety for use in fluorine-19 NMR and/or MRI studies. The perfluoro-t-butyl (PFTB) moiety,

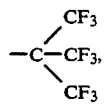

is an excellent reported group for fluorine-19 NMR/MRI. It is a source of nine magnetically equivalent fluorine nuclei which generate a single intense resonance for each detection in spectroscopy or imaging. This signal is a sharp singlet, not split by neighboring nuclei or spread over a wide frequency range and eliminates any change of ghost images which might arise from multiple resonances. These spectral properties ensure a maximum signal-to-noise ratio (S/N) for readily detecting this moiety. The foregoing allows either reduction in the concentration of the derivatized compound, ability to use MRI instruments with lower field strengths, a reduction in imaging times, or a combination of the foregoing as a result of this moiety producing a single, sharp, intense resonance.

Additionally, the PFTB moiety-containing compounds may be utilized to determine oxygen concentration in aqueous solutions present in animate and inanimate objects.

2 Claims, 8 Drawing Sheets

100 MILLIMOLAR
PTFB
67 PPM SINGLET

OTHER PUBLICATIONS

B. L. Dyatkin et al., Uspekhi Khimii, vol. 45, p. 1205, 1976.

K. Yamada et al., "In vivo F-19 NMR Imaging and the Influence of Oxygenation on Relaxation Time", Sci. Rep. Res. Inst. Tohoku Univ., -C, vol. 33, Nos. 1-4, pp. 44-48 (1986).

J. Fraham et al., "Localized Proton NMR Spectroscopy in Different Regions of the Brain in Vivo. Relaxation Times and Concentrations of the Cerebral, Metabolites", Magnetic Resonance in Medicine, vol. 11, pp. 47-63 (1989).

D. M. Freeman et al., "Rapid [19]F Magnetic Resonance Imaging of Perfluoro-octyl Bromide In Vivo", Magnetic Resonance Imaging, vol. 6, pp. 61-64, 1988.

R. L. Nunnally et al, "Flourine-19 NMR Spectroscopy and Imaging Investigations of Myocardial Perfusion and Cardiac Function", Magnetic Resonance Imaging, vol. 3, pp. 399-405, 1985.

W. M. Chew et al., "Spin-Echo Fluorine Magnetic Resonance Imaging at 2T: In Vivo Spatial Distribution of Halothane in the Rabbit Head", Magnetic Resonance Imaging, vol. 5, pp. 51-56, 1987.

T. Nakada et al., "F-19 NMR Imaging of Glucose Metabolism in the Rabbit", Radiology, vol. 168, pp. 823-825, 1988.

A. V. Ratner et al., "Detection of Tumors with [19]F Magnetic Resonance Imaging", Investigative Radiology, vol. 23, pp. 361-364, May 1988.

M. E. Phelps, "Emission Computed Tomography", Seminars in Nuclear Medicine, vol. 7, No. 4, Oct. 1977.

M. E. Phelps et al., "ECAT: A New Computerized Tomographic Imaging System for Positron-Emitting Radiopharmaceuticals", The Journal of Nuclear Medicine, vol. 19, No. 6, pp. 635-647, 1978.

Amersham Corp. Technical Brochure: "Introduction to SPECT Brain Imaging with Ceretec TM (technetium Tc99m exametazime injection)", Printed Apr. 1989.

Medi-Physics, Inc. Technical Brochure: "SPECTamine © Iofetamine HCl I123 Injection", Issued Dec. 1987, ©1988.

N. N. Becker et al., Abstracts 7th Annual Meeting Soc. Magn. Reson. Med., p. 447 (1988).

B. L. Dyatkin et al., Russian Chemical Reviews, vol. 45, No. 7, pp. 607-614 (1976) (translated from Upsekhi Khimii, vol. 45, pp. 1205-1221 (1976)).

G. N. Holland et al., J. Magn. Reson., vol. 28, pp. 133-136 (1977).

I. L. Knunyants et al., Synthesis of Flyoroorganic Compounds, Springer-Verlag, N.Y., pp. 5 and 12 (1985).

E. McFarland et al., Jr. Comput. Assist. Tomogr., vol. 9, No. 1, pp. 8-15 (Jan./Feb. 1985).

J. Weichert et al., Abstracts 7th Annual Meeting Soc. Magn. Reson. Med., p. 484 (1988).

Weichert et al., Abstracts 8th Annual Meeting Soc. Magn. Reson. Med., p. 330 (1989; after filing date).

A. M. Wyrwicz et al., J. Magn. Reson., vol. 69, No. 3, pp. 572-575 (Oct. 1, 1986).

Y. V. Zeifman et al., Russian Chemical Reviews, vol. 53, No. 3, pp. 256-273 (1984) (translated from Uspekhi Khimii, vol. 53, pp. 431-461 (1984)).

Abstract, vol. 79, 1973, p. 408; Abstract No. 4760b.

Gopal N. Saha, *Fundamentals of Nuclear Pharmacy* (2nd Ed.), Springer-Verlag New York, Inc. (C) 1984, pp. 87-97 (Methods of radioiodination), pp. 116-118 (radioiodine labeled albumin, cholestrol and fibrinogen).

C. A. Otto et al., "Radiochemistry and Radiopharmaceuticals," *J. Nucl. Med.*, 22:613-618, 1981 (radioiodinated fatty acids).

Principles of Radiopharmacology, vol. 1, CRC Press, Inc. Boca Raton, Fla. (Editor: Lelio G. Colombetti, Sc.D.) (C) 1979, pp. 30-35 and 40-43 (labeling techniques), pp. 193-206, 208-217, 221, 223-224, and 227-250 (various halogenated compounds, e.g., amino acids at pp. 211-212, sugars at p. 213, fatty acids at p. 213, and steroids at p. 228).

Whitmore, Organic Chemistry, D. Van Nostrand Company, Inc., N.Y., N.Y. (C) 1937, pp. 548-579 (Carbohydrates, Glucocides, Saccharides).

Morrison and Boyd, Organic Chemistry (2nd Ed.), Allyn & Bacon, Inc., (C) 1966, pp. 708-709.

Smart et al., "Stable Perfluoroalkyl Carbanion Salts", J. Am. Chem. Soc., vol. 108, pp. 4905-4907 (1986).

Weigert and Mahler, "NMR Parameters of the Individual Fluorines of the Triflurormethyl Group", J. Am. Chem. Soc., vol. 94, pp. 5314-5318 (1972).

Huang et al., "Synthesis of Unusual Perfluorocarbon (List continued on next page.)

OTHER PUBLICATIONS

Ethers and Amines Containing Bulk Perfluorocarbon Groups: New Biomedical Materials", J. Org. Chem., vol. 53, pp. 78-85 (1988).

*The Chemistry of Brain Metabolism in Health and Disease* by J. H. Quastel et al., published by Charles C. Thomas, Springfield, Illinois ©1961, pp. 41-52.

"N-Isopropyl-[$^{123}$I] p-Iodoamphetamine: Single-Pass Brain Uptake and Washout: Binding To Brain Synaptosomes; And Localization in Dog and Monkey Brain," H. S. Winchell et al., *The Journal of Nuclear Medicine*, vol. 21, No. 10, pp. 947-952 (1980).

"Development of I-123-Labelled Amines For Brain Studies: Localization of I-123 Iodophenylalkyl Amines In Rat Brain", H. S. Winchell et al., *The Journal of Nuclear Medicine*, vol. 21, No. 10, pp. 940-946 (1980).

"Specific Carcino-Embryonic Antigens of the Human Digestive System," P. Gold et al, *Journal of Exploratory Medicine*, 122:467-81 (1965).

V. T. DeVita et al, *Principles and Practice of Oncology*, published J. D. Lippincott Company (Copyright 1989) at pp. 316-321.

"Tumor Localization of Radio Labelled Antibodies Against Carcino-Embryonic Antigen in Patients With Carcinoma," J. Mach et al, *The New England Journal of Medicine*, vol. 303, No. 1 pp. 5-10 (1980).

Gopal B. Saha, *Fundamentals of Nuclear Pharmacy* (2nd Ed.), Springer-Verlag New York, N.Y., 1984, pp. 96-99 and 110.

"Iodine-131 labeled fibronectin: Potential Agent For Imaging Atherosclerotic Lesions and Thrombus," A. Uehara et al, *The Journal of Nuclear Medicine*, vol. 29, No. 7, pp. 1264-1267 (1988).

*Radio Pharmaceuticals, Structure-Activity Relationships*, Edited by R. P. Spencer, published by Grune an Stratton, Inc., New York, N.Y. ©1981, particularly Chapter 23 "Structure-Activity Relationship In Cell Labeling" by M. L. Thakur et al, pp. 505-517.

G. W. Anderson et al., "The Use of Esters of N-hydroxysuccinimide In Peptide Synthesis," Journal of the American Chemical Society, vol. 86, pp. 1839-1942 (1964).

G. W. Anderson et al., "Synthesis of N-hydroxysuccinimide Esters of Acyl Peptides by the Mixed and Anhydride Method," Journal of the American Chemical Society, vol. 89, p. 178 (1967).

J. V. Staros et al., "Enhancement by N-hydroxysulfosuccinimide of Water-Soluble Carbodiiamide Mediated Coupling Reactions," Analytical Biochemistry, vol. 156, pp. 220-222 (1986).

FIG. 1(a)

100 MILLIMOLAR PTFB
67 PPM SINGLET

FIG. 1(b)

10 mM REFERENCE (CFCl₃)

10 MILLIMOLAR PTFB
S/N = 100 TO 1

FIG. 1(c)

1 MILLIMOLAR PTFB
S/N = 10 TO 1

FIG. 1(d)

0.1 MILLIMOLAR PTFB
S/N = 2 TO 1

0   50   100 PPM

PERFLUORO-T-BUTYL-CONTAINING COMPOUNDS FOR USE IN FLUORINE-19 NMR AND/OR MRI

This application is a division of application Ser. No. 07/762,445, filed Sep. 19, 1991 now U.S. Pat. No. 5,234,680, which is a division of application 07/388,049, filed Jul. 31, 1989, now U.S. Pat. No. 5,116,599.

FIELD OF THE INVENTION

This invention relates, in general, to nuclear magnetic resonance techniques (NMR). More particularly, it relates to NMR and MRI (magnetic resonance imaging) utilizing fluorine as a detected element. In one aspect, this invention relates to derivatized biological compounds containing at least one perfluoro-t-butyl moiety as the fluorine reporter group. In a further aspect, this invention is directed to the preparation and use of such derivatized biological compounds.

BACKGROUND OF THE INVENTION

Non-invasive techniques in medical diagnoses have expanded dramatically in the past 10 years. Nuclear magnetic resonance of hydrogen has already proven to be well suited for the depiction of anatomy with excellent spatial resolution. However, this technique suffers from long acquisition times and is not amenable to obtaining metabolic information.

Positron emission tomography (PET), on the other hand, has the ability to use radiolabeled natural metabolic substrates in tracer concentrations to assess basic metabolic activity. However, this technique possesses poor spatial resolution and requires an on-site cyclotron. PET relies on ionizing radiation for its operation.

Fluorine($^{19}$F) NMR/MRI shows promise but also poses problems in its initial stages of development toward practical application. Fluorine-19 has a high NMR sensitivity (about 83% that of hydrogen), negligible biological background, a resonance frequency only 6% lower than hydrogen, a spin of $\frac{1}{2}$, and 100% natural abundance. Hydrogen NMR, MRI equipment may also be used for detection of fluorine-19. Commercially available fluorinated compounds used for MRI or NMR studies generate a wide range of resonance frequencies resulting from differences in local electron environments affecting the fluorine nucleus. Several dozen compounds have been used in in vivo studies either as inert agents or metabolic agents. The inert agents include perfluorinated compounds such as perfluoro-tri-n-butyl amine, Fluosol TM perfluorocarbon mixture (a mixture of perfluorotripropylamine and perfluorodecalin) (distributed by Alpha Therapeutic Corp., Los Angeles, Calif. for Green Cross Corp. Osaka, Japan) and perfluorooctyl bromide and fluoromethanes and fluoroethanes such as trifluoromethane, chlorodifluoromethane and halothane. Metabolic agents include monofluorinated aliphatics such as 5-fluorouracil and fluorodeoxy glucose and fluorinated aromatics, such as trifluoromethyl aromatics and monofluoro aromatics.

These compounds fail to provide fluorine in sufficient numbers (for example, 5-fluorouracil and 3-fluoro-3-deoxy-D-glucose) or may contain broad multiple peaks (for example, perfluorodecalin and perfluorotri-n-butylamine) both being detrimental to imaging. The combination of chemical shift effects and decreased integrity of split signals (multiple peaks) reduces the detectability of any signal, thereby requiring longer imaging times. Present animal studies require greater than one hour acquisition time for fluorine-19 MRI studies even at high concentrations of the fluorinated compound utilized, for example, 2.4M in rabbits of standard size, representing 30% blood replacement. D. Eidelberg et al., "$^{19}$F NMR Imaging of Blood Oxygenation in the Brain," *Magnetic Resonance in Medicine*, vol. 6, pages 344-352 (1988). This lengthy process could be shortened and concentration reduced if a stronger signal emanated from the sample.

Though perfluorination of biological compounds would increase the number of fluorines therein, the chemical and biological behavior of such perfluorinated compounds, particularly metabolic compounds, would likely not be equivalent to their non-fluorinated condition, i.e., natural compound. Further, such perfluorinated compounds would suffer from decreased intensity of split signals.

There has been much interest in the use of PFCs as oxygen carrying agents. In addition to their use as blood substitutes, experimental work has shown their efficiency in delivering oxygen to ischemic tissue and hence their potential as therapeutic agents in the treatment of cerebral and myocardinal ischemia. These compounds have also found application in NMR vascular imaging. PFCs contain a high concentration of $^{19}$F atoms and can be imaged with machines designed for hydrogen protons with only minor modifications in tuning As $^{19}$F is virtually absent from biological tissues, intravenously infused PFC emulsions are an excellent vascular marker and may be used to image the perfusion of tissues of high vascularity. There are, however, a number of problems which limit the signal-to-noise ratio (SNR) of PFC images. First, the concentration of $^{19}$F is low relative to $^1$H concentration (around 2.4M in blood after 30% volume replacement compared with a $^1$H concentration of 80M). Second, infused PFCs have short transverse relaxation times ($T_2$'s) and therefore the NMR signal decays rapidly after it has been produced. In addition PFCs have a spectrum with several peaks at different resonant frequencies giving rise to the misregistered superimposition of images from each peak. Eliminating this chemical-shift artifact often involves loss of the signal from the suppressed portion of the spectrum. Nonetheless, because of the relatively high intrinsic vascularity of the mammalian cerebral cortex D. Eidelberg et al. thought that in-vivo $^{19}$F brain imaging with infused PFC might be feasible.

PFCs have the added advantage of potential use as indicators of intravascular oxygenation. Molecular oxygen is paramagnetic and enhances spin-lattice relaxation by dipole-dipole interactions in such a way that the rate 1/T. increases linearly with $pO_2$ (6). Pairs of $^{19}$F partial saturation spin-echo (PSSE) images of varying repetition time ($T_R$) may be used to compute a $T_1$ map and the $1/T_1$ vs $pO_2$ calibration line may then be applied to calculate $pO_2$ in vessels (8). A limitation of PFCs is the multi-resonnant signals resulting from non-equivalent fluorine nuclei. Use of inert compounds with 2 to 4 reporter groups, containing 18 to 36 fluorine atoms would greatly enhance the sensitivity of measurement of regional $O_2$ concentration. Such a technique made possible in humans would clearly have important ramifications in all organ systems.

Therefore, there exists a need to provide a fluorine-derivatized compound for introducing fluorine to a site or process specific biological compound which would not only allow visualization of a given organ, but also provide metabolic data without suffering the aforementioned disadvantages of known compounds when NMR or MRI studies are performed using same.

SUMMARY OF THE INVENTION

Accordingly, the present invention is directed to biological compounds derivatized so as to contain at least one perfluoro-t-butyl moiety for use in fluorine-19 NMR and/or MRI studies. The perfluoro-t-butyl (PFTB) moiety, is an excellent reporter group for fluorine-19 NMR/MRI. It is a source of nine magnetically equivalent fluorine nuclei which generate a single intense resonance for easy detection in spectroscopy or imaging. This signal is a sharp singlet, not split by neighboring nuclei or spread over a wide frequency range and eliminates any change of ghost images which might arise from multiple resonances. These spectral properties ensure a maximum signal-to-noise ratio (S/N) for readily detecting this moiety. The foregoing allows either reduction in the concentration of the derivatized compound, ability to use MRI instruments with lower field strengths, a reduction in imaging times, or a combination of the foregoing as a result of this moiety producing a single, sharp, intense resonance.

Additionally, the PFTB moiety-containing compounds may be utilized to determine oxygen concentration in aqueous solutions present in animate and inanimate objects.

BRIEF DESCRIPTION OF THE DRAWINGS

FIGS. 1(a)-(d) are fluorine-19 NMR spectra of 1,1,1-trifluoro-2,2-bis(trifluoromethyl)-hexane, a PFTB moiety-containing compound, in CDCl$_3$ in concentrations of 100 millimolar PFTB, 10 millimolar PFTB, 1 millimolar PFTB and 0.1 millimolar PFTB, respectively, using a 10 millimolar (10 mM) CFCl$_3$ in CDCl$_3$ reference (an internal standard).

DETAILED DESCRIPTION OF THE INVENTION

Figure 2:
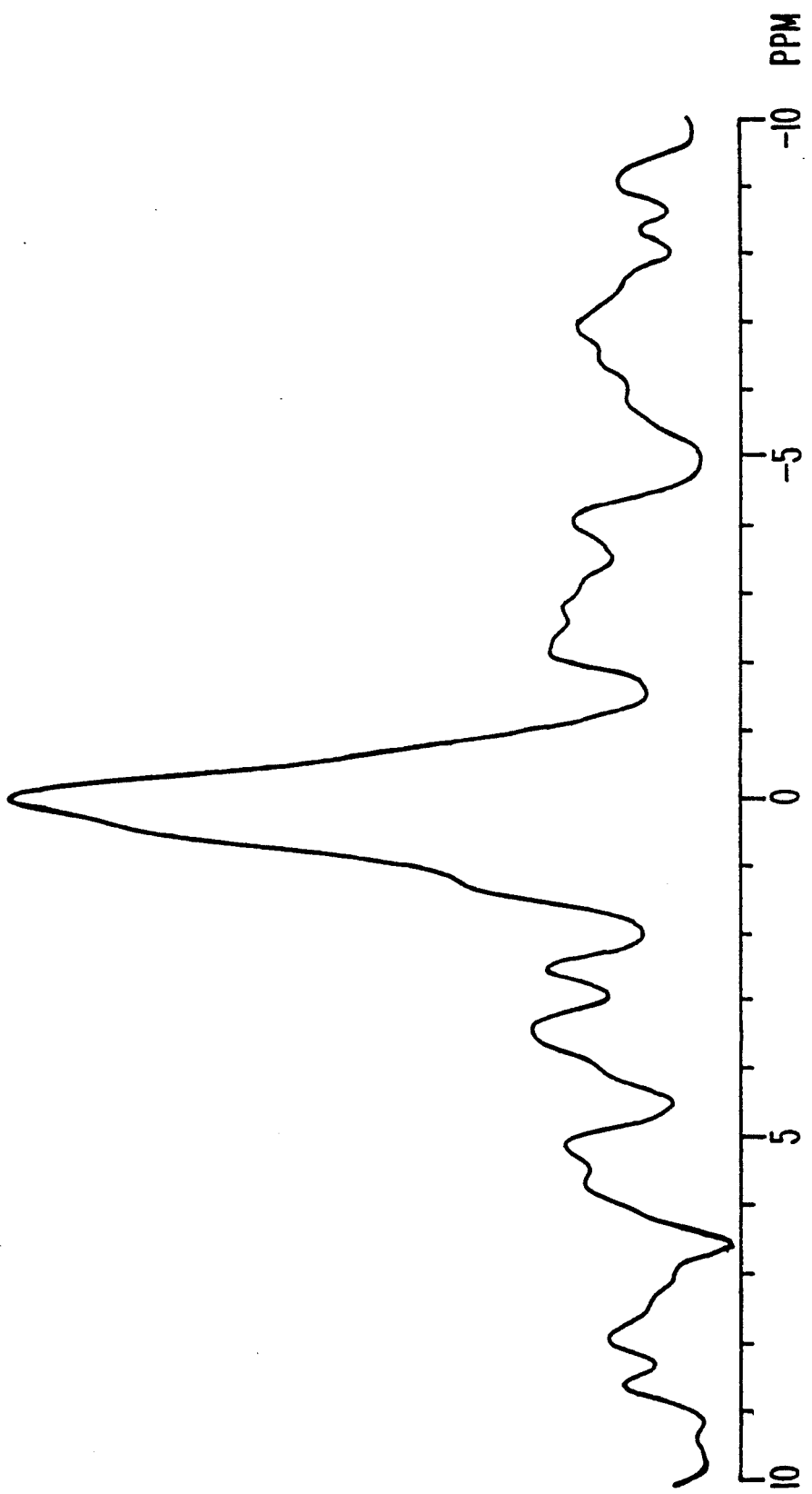
FIG. 2 presents a fluorine-19 NMR spectrum of a PFTB moiety labelled fatty acid used for detecting metabolic activity in the chest of a rabbit in the area of the heart.
Figure 3:
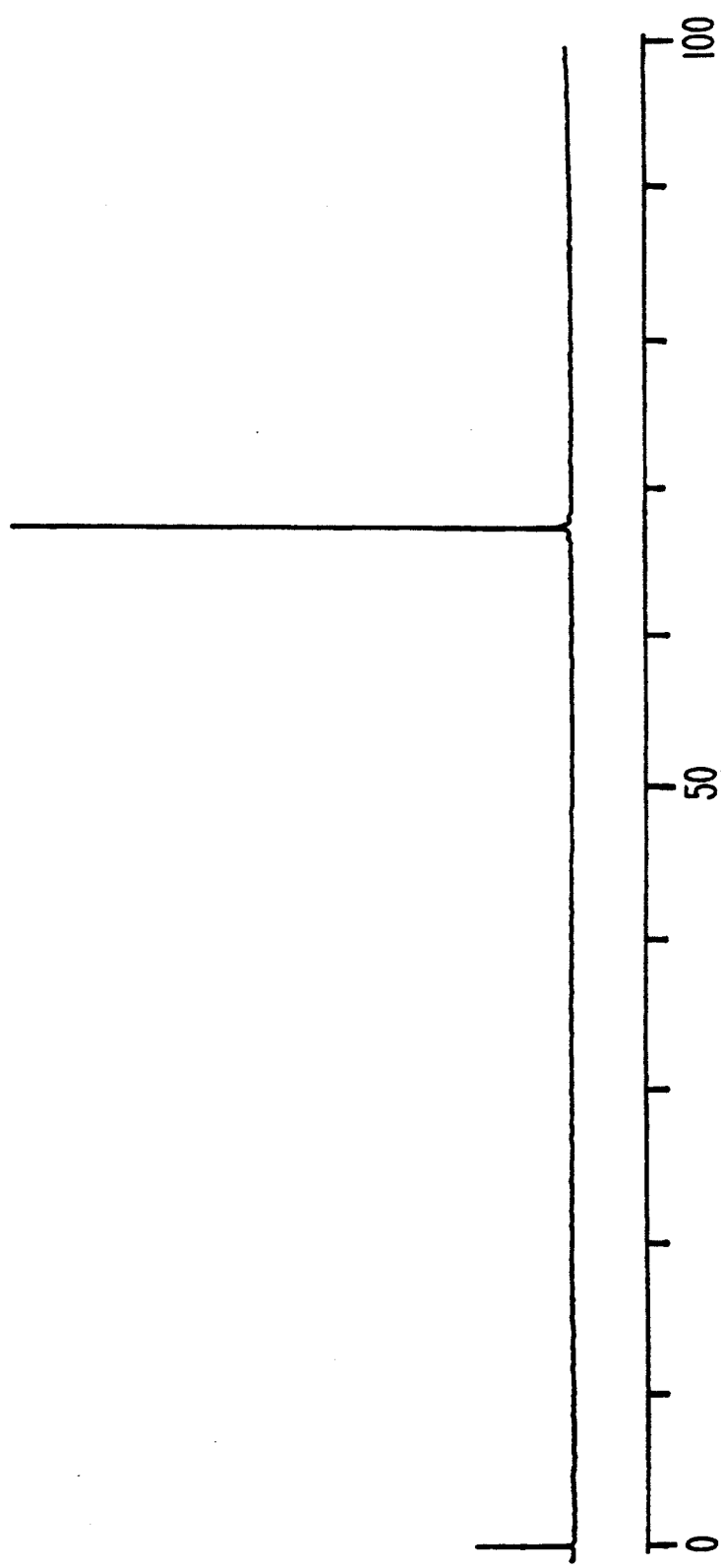
FIG. 3 presents a fluorine-19 NMR spectrum of 10 mM concentration of the PFTB moiety-containing compound of Example 1 herein, i.e., 1,1,1-trifluoro-2,2-bis(trifluoromethyl)hexane.
Figure 4:
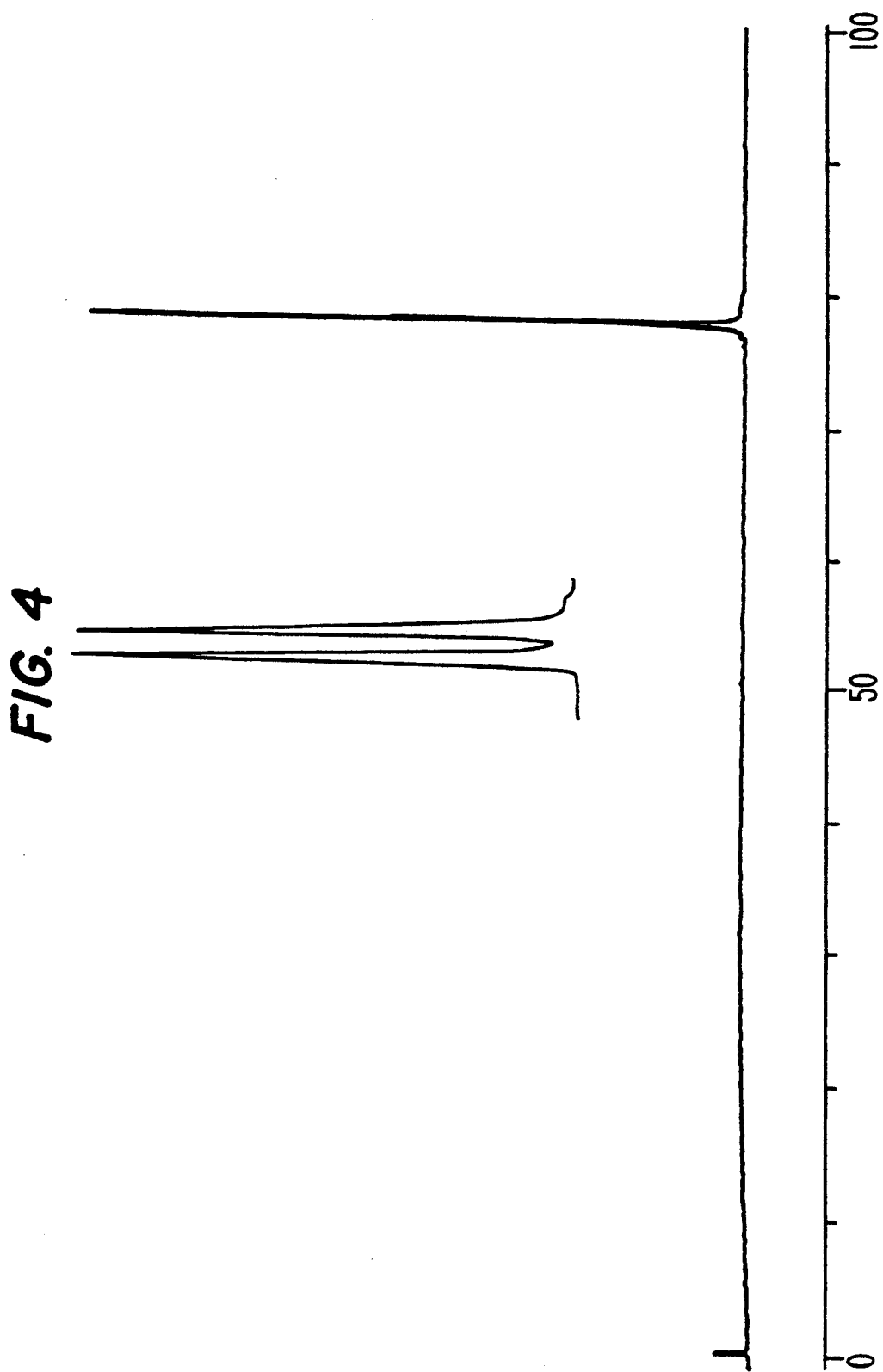
FIG. 4 presents a fluorine-19 NMR spectrum of a 100 mM concentration of halothane (prior art compound).
Figure 5:
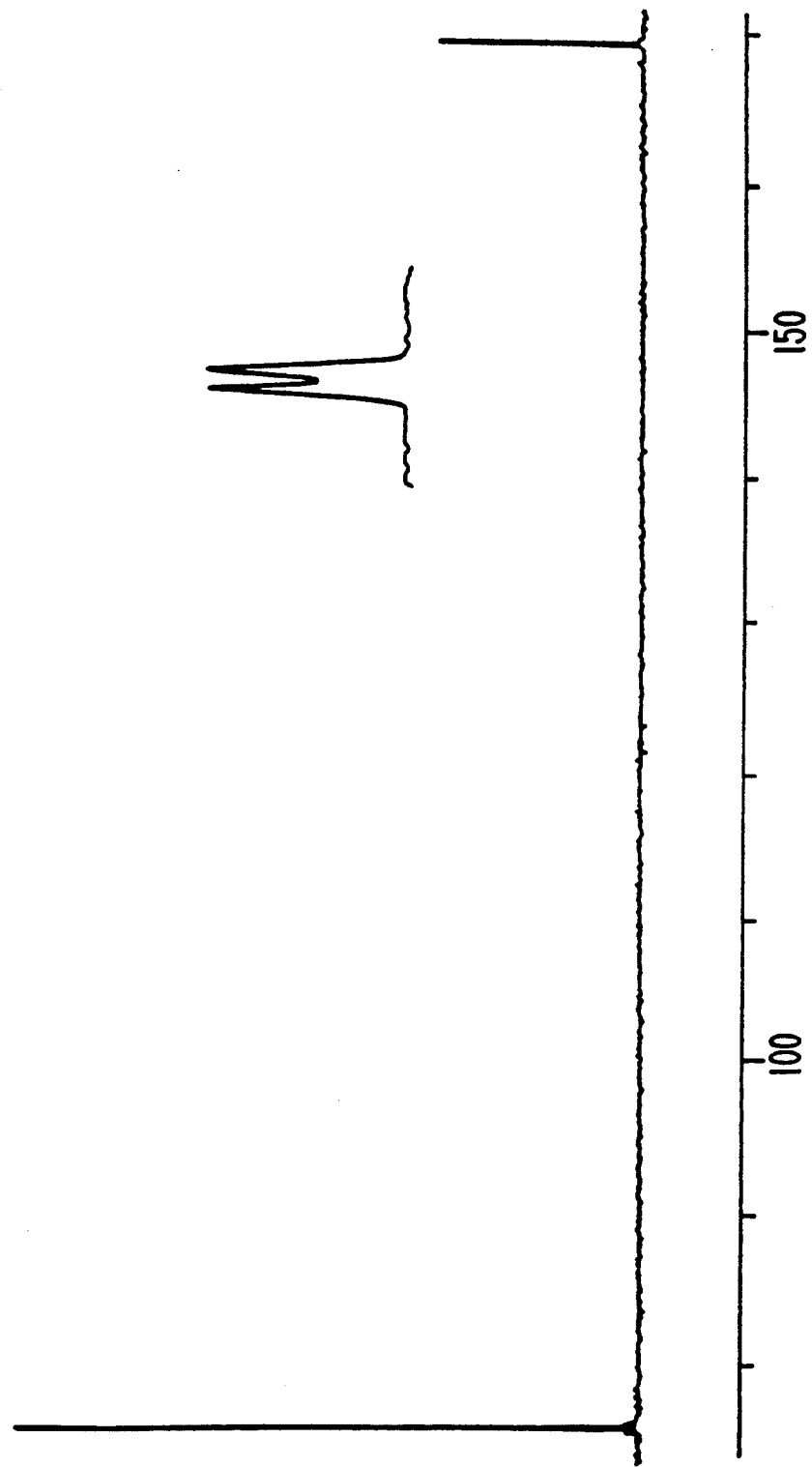
FIG. 5 presents a fluorine-19 NMR spectrum of a 150 mM concentration of 5-FU (prior art compound).
Figure 6:
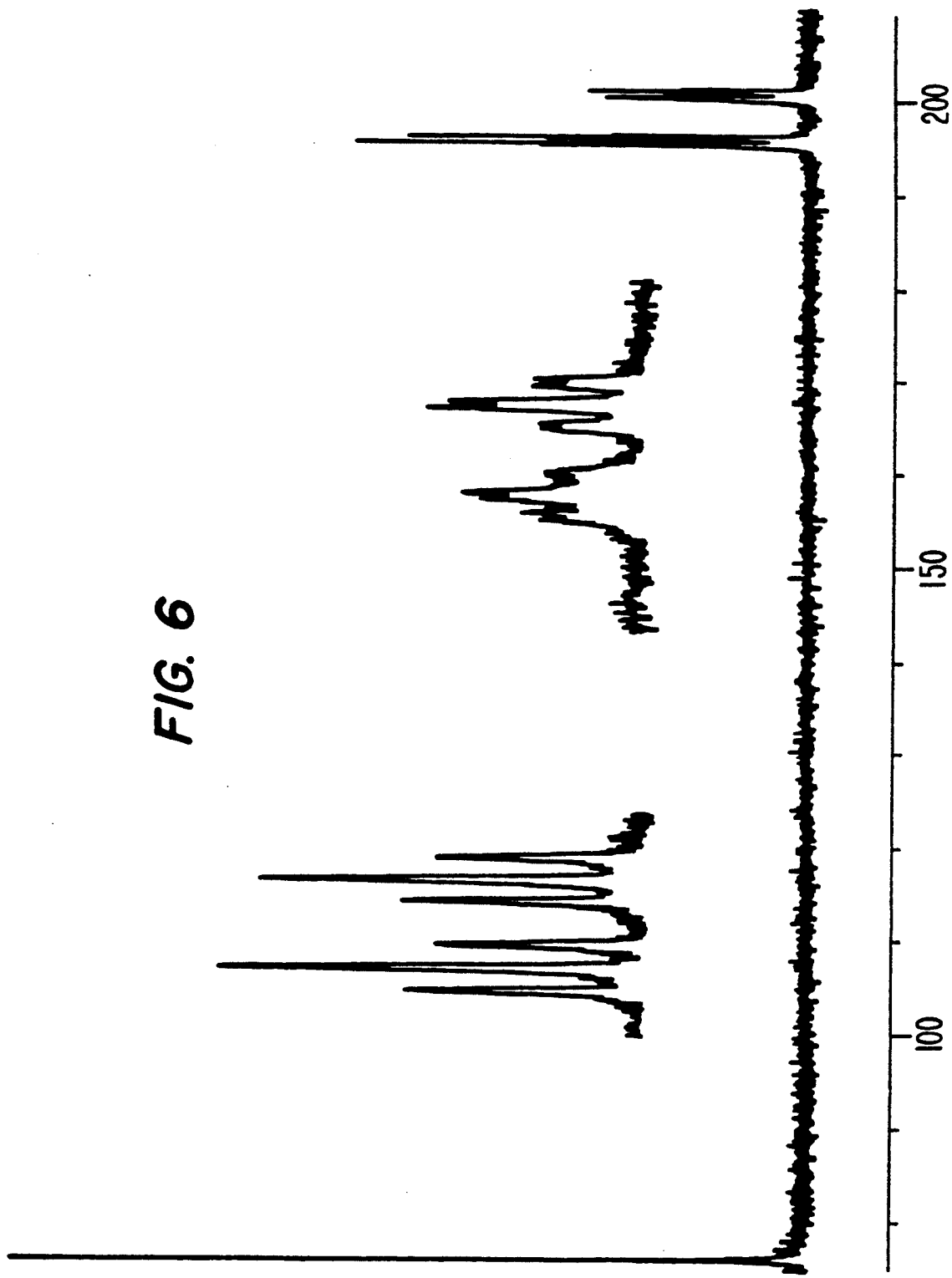
FIG. 6 presents a fluorine-19 NMR spectrum of a 200 mM concentration of 3-FDG (prior art compound).
Figure 7:
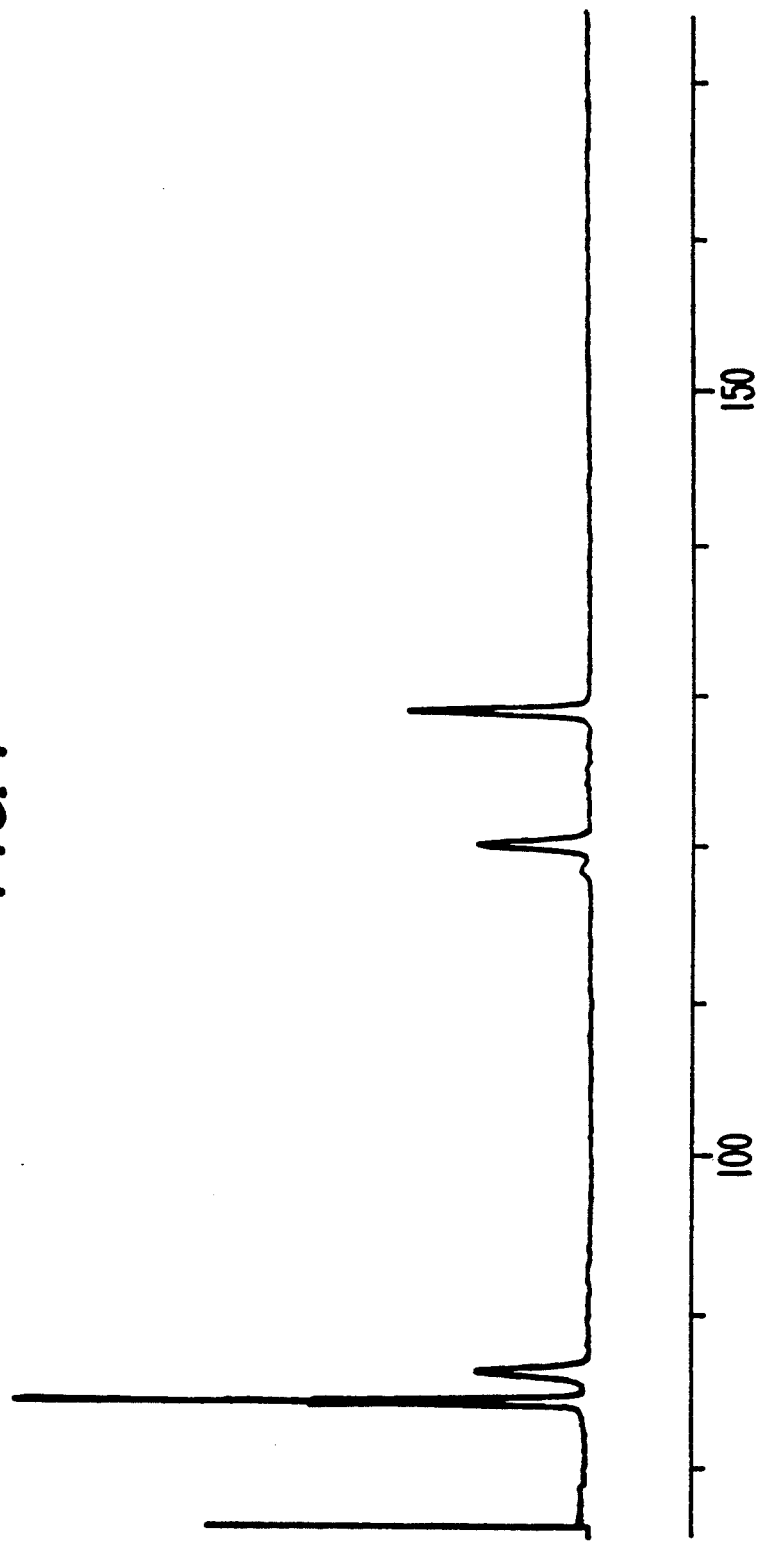
FIG. 7 presents a fluorine-19 NMR spectrum of a 3M concentration of FC-43 (prior art compound).
Figure 8:
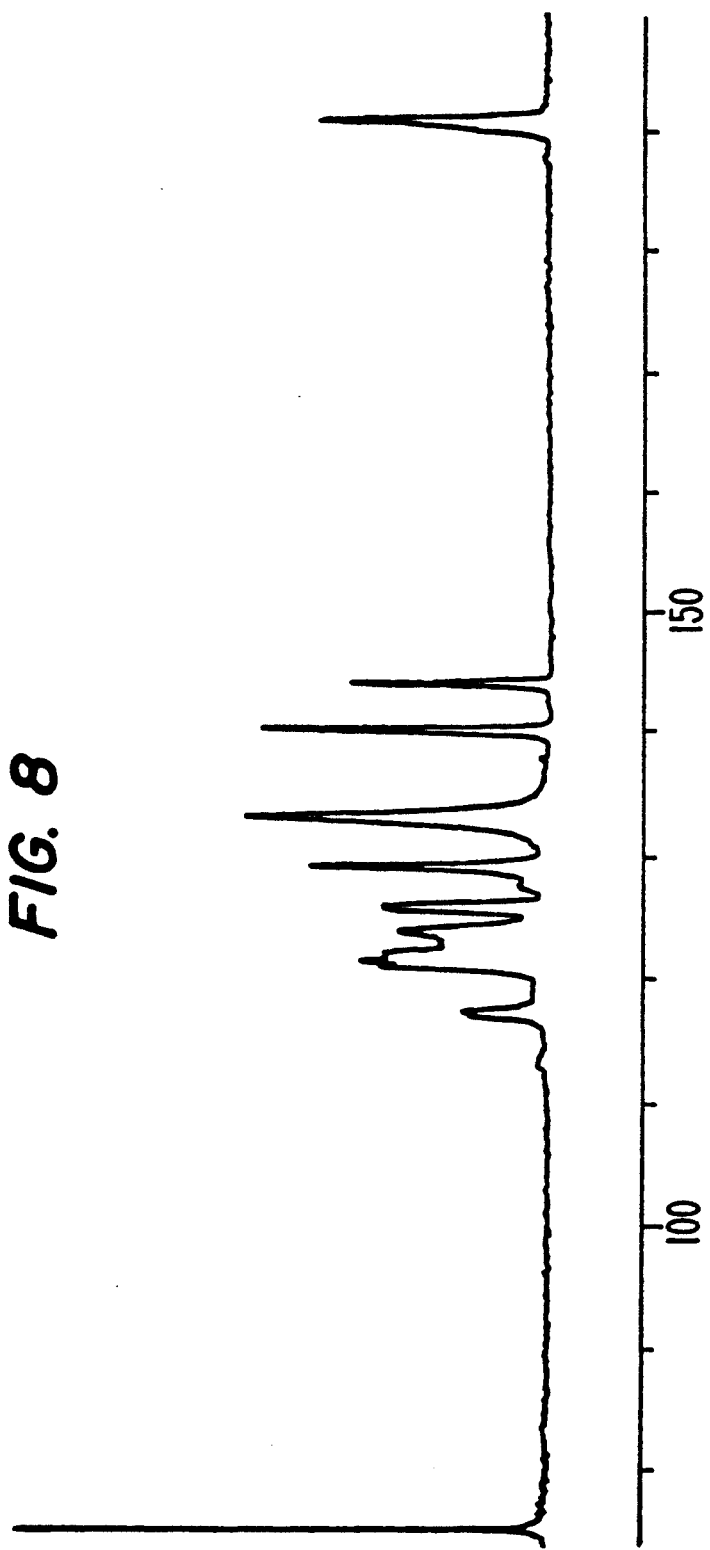
FIG. 8 presents a fluorine-19 NMR spectrum of 4M concentration of perfluorodecalin (prior art compound).

This invention is based on the discovery that the perfluoro-t-butyl group is an excellent general reporter group for fluorine-19 NMR/MRI. It is the source of nine magnetically equivalent fluorine nuclei which generate a single, sharp, intense resonance for easy detection in spectroscopy or imaging. This signal is a sharp singlet, not split by neighboring nuclei or spread over a wide frequency range. These spectral properties ensure a maximum signal-to-noise ratio (S/N) for readily detecting this moiety.

The perfluoro-t-butyl (PFTB) moiety may be introduced to a host biological compound which may be an inert agent or a metabolic agent. Properly positioned within the host compound, the PFTB moiety will act as an NMR/MRI detectable tag or reporter group, without appreciably affecting the normal biochemical processes characteristic of the host (unaltered) compound (biomolecule).

Perfluorinated carbon compounds tend to be very chemically and biochemically inert as multiple fluorines possessing great electro-negativity surround a carbon backbone with electron density and shield the carbon backbone from nucleophilic attack. The carbon-fluorine bond is very strong and resists cleavage even in harsh chemical environments; the trifluoromethyl group (CF$_3$) is especially noteworthy in its chemical stability. The key to perceiving potential toxicity in fluorinated compounds is to evaluate the structure's propensity toward fluoride ion elimination. There is no readily available mechanism by which the perfluorinated tert-butyl group can eliminate or release fluoride and we predict minimal toxicity for this subunit.

Thus, it is believed that the PTFB moiety embodies the desirable properties of high fluorine content for easy imaging with minimal aberration of the overall geometry and normal biochemisty of the host molecule upon which it is attached. Furthermore, once suitably attached to a host compound, for example, a biologically active or inert molecule, the PFTB moiety is believed not to induce undesirable toxicity.

We have discovered that submillimolar concentrations of PFTB moiety-containing fatty acids can be readily detectable by fluorine-19 NMR spectroscopy, well within the range of naturally occurring analogs. Additionally, the PFTB moiety signal is not reduced through chemical shift effects. Thus, it is believed that host molecules containing at least one PFTB moiety will be more sensitive to metabolic imaging.

The chemical synthesis and manner of incorporating the PFTB moiety onto the host compound may be accomplished in any suitable manner. One such method of generating the PFTB moiety follows the organofluorine synthesis reported in the chemical literature by I. L. Knunyants and coworkers at the Institute of Organo-elemental Compounds in Moscow. See, Knunyants, I. L., Yakobson, G. G., *Syntheses of Fluoroorganic Compounds*, Springer-Verlag, New York, 1985; Zeifman, Y. V., Ter-Gabrielyan, E. G., Gambaryan, N. P. Knunyants, I. L., Uspekhi Khimii, 1984, Vol. 53, p. 431; and Dyatkin, B. L., Delyagina, N. I., Sterlin, S. R., Uspekhi Khimii; 1986, Vol. 45, p. 1205; which are herein incorporated by reference. Therein, perfluoroisobutylene is a source of all four carbons and eight of the nine fluorines which make up the reporter group. Perfluoroisobutylene (I) in the presence of a fluoride ion source (for example, CsF) forms a stabilized carbanion intermediate (II). The stabilized carbanion intermediate II reacts readily with a variety of alkyl halides (RX) to form PFTB moiety substituted compounds (III) as shown in the following equation.

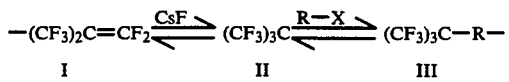

The synthesis allows a fluorinated reporter group, i.e., a PFTB moiety, to be readily incorporated onto the backbone of a biologically active host molecule, such as a fatty acid, sugar, amino acid, or a steroid, or a biologically inert hose molecule, such as plasma components and brain perfusion molecules. Thus, the host molecule or compound would be the R group in Equation A.

In Equation A above, the X group represents a good leaving group, such as a halide or a sulfonyl group. The halide may be fluoride, chloride, bromide, or iodide. The sulfonyl group includes, but is not limited to, mesyl (methylsulfonyl), tosyl (tolylsulfonyl), and triflyl (trifluoromethylsulfonyl).

For example, such host compounds (R) may be chemically modified to incorporate a halide group (X), such as bromide, and then subjected to the foregoing reaction scheme to incorporate the PFTB moiety. Such can be effectively performed by either utilizing an existing hydroxyl group or incorporating a hydroxyl group at the desired location on the host molecule (R) and then substituting a halide (X) for the hydroxyl group. Such substitution schemes are well known to those skilled in the art.

Sugar compounds include, but are not limited to, sugars, sugar acids, sugar alcohols, and deoxy sugars. Sugars include, but are not limited to, D-glucose, ribose, fructose, and mannose. Sugar acids include, but are not limited to, D-gluconic acid, D-delta-gluconolactone, D-delta-glucuronolactone, D-glucuronic acid, L-ascorbic acid, and L-dehydroascorbic acid. Sugar alcohols include, but are not limited to, L-sorbitol, D-mannitol, glycerol, and myo-inositol. Deoxy sugars include, but are not limited to, 2-deoxy-D-ribose, L-rhamnose, L-fucose (6-deoxy-L-galactose), and glucose-6-phosphate.

In general, sugars are used variably by the body depending on physiological stress and pathologic state thereof. Organs of interest would be the heart, brain and liver. Glucose is the sole substrate for monitoring brain metabolic activity. 2-deoxy-alpha-D-glucose is transported like a glucose but not metabolized by the body. Thus, labeled sugars are contemplated for use in monitoring brain metabolic activity. Labeled sugar acids are contemplated for use in monitoring carbohydrate metabolism. Labeled sugar alcohols are contemplated for use in lipid analysis. Labeled deoxy sugars, such as glucose-6-phosphate, are contemplated for use in monitoring liver activity.

Fatty acids may include acids having from about 4 to about 20 carbons. Examples of such fatty acids are palmitoleic acid (16 carbons), oleic acid (18 carbons), linoleic acid (18 carbons), and linolenic acid (18 carbons), and arachidonic acid (20 carbons). In general, fatty acids are used as energy substrates (70% of the energy used by the resting heart is provided by utilizing fatty acids).

Amino acids include, but are not limited to, arginine, histidine, glutamine, glutamic acid, and proline. Labeled amino acids are contemplated as liver function probes. i.e., for use in the determination of sites of amino acid catobolism.

Steroids include, but are not limited to, lanosterol, cholesterol, corticosterone, aldosterone, estrone, beta-estradiol, testosterone, and progesterone. In general, a steroid's function varies widely according to its structure. Labeling thereof would be useful in the determination of the distribution thereof in various organs and pathologic states thereof.

Plasma components include, but are not limited to, erythrocytes (red blood cells), leucocytes (white blood cells), platelets, serum albumin, fibrinogen, neutrophiles, and prothrombin. Labeled erythrocytes are contemplated for use as blood pool imagery agents similar to $^{99m}$Tc labeled red blood cells used in nuclear cardiology. Labeled leucocytes are contemplated for use in detecting the distribution of white blood cells particularly since such cells, concentration increases in an injury site or disease infected areas of the body. Labeled platelets would be used as a thrombus detector since platelets are utilized in blood clot regulation. Labeled serum albumin would also be used as a blood pool agent. Labeled fibrinogen and prothrombin would be utilized in the detection of thrombus. Labeled neutrophiles would be utilized in the detection of damaged tissue.

Brain perfusion agents such as Iofitamine I$^{123}$-N-isopropyl-p-iodo amphetamine hydrochloride) are presently utilized in nuclear medicine brain scanning in the evaluation of stroke. Such a compound could be modified in one of two ways. The first would be to replace the radioactive iodine component (I-123) thereof with the PFTB moiety hereof; and the other by incorporating a PFTB moiety thereon, thereby having a dual function compound for cross comparison.

The PFTB moiety-containing compounds of the present invention may be used to determine oxygen concentrations in aqueous fluids in animate and inanimate objects using fluorine-19 NMR/MRI by the effect of oxygen on the longitudinal relaxation time of fluorine therein. The PFTB moiety-containing compounds of the present invention are believed to provide enhanced detection of oxygen concentration over compounds presently utilized. Thus, the PFTB moiety-containing compounds of the present invention would be substituted for the compounds utilized in D. Eidelberg et al., "19F NMR Imaging Blood Oxygenation in the Grain", *Magnetic Resonance in Medicine*, vol. 6, pages 344–352 (1988) and in K. Yamada et al., "In vivo F-19 NMR Imaging and the Influence of Oxygenation on Relaxation Time", *Sci. Rep. Res. Inst. Tohoku Univ.*, -C, vol. 33, Nos. 1–4, pages 44–48 (1986).

EXAMPLE 1

Determine the Lower Limits of Detectability of the PFTB Fluorine Resonance Signal (Test the Ease of MRI and NMR Detection)

In this example, a PFTB moiety-containing compound was synthesized according to Equation A and proceeded smoothly to give gram quantities of material. This material was utilized to determine the lower limits of detectability of the PFTB fluorine-19 resonance signal as a function of concentration.

The PFTB moiety-containing compound prepared was 1,1,1-trifluoro-2,2-bis(trifluoromethyl)-hexane. This material was prepared as follows.

6.3 mL (10 g; 50 mmoles) perfluoroisobutylene (CAUTION! highly toxic) were condensed into a heterogeneous mixture of 7.6 g (50 mmoles) cesium fluoride stirring in 20 mL of dry diglyme. A yellow color developed within the reaction mixture, attributed to carbanion formation. After 2 hours of mild heating (about 50° C.) and stirring, 6.9 g (50 mmoles) 1-bromobutane were added. Upon this addition of alkyl halide, much milky precipitate was observed. The reaction was allowed to stir several hours (about 4 hours), then the low boiling product was isolated by attaching a condenser to the reaction set-up and heating to 150° C. Thus 9.8 g of a clear, colorless liquid were distilled from the crude reaction mixture. Further purification by fractional distillation yielded 8.0 g (58% overall yield) of liquid with a boiling point of 108° C. Confirmation of structure $(CF_3)_3CCH_2CH_2CH_2CH_3$, was provided by proton and fluorine-19 NMR with supporting data from the chemical literature (Knunyants, I. L., Yakobson, G. G., *Synthesis of Fluoroorganic Compounds*, Springer-Verlag, N.Y., 1985).

Spectroscopic data (see FIGS. 1(a)–(d), acquired on an IBM NR/80 operating at 75.39 MHz for fluorine-19 NMR) obtained on this compound supports the basic premise that the nine equivalent fluorines of the PFTB moiety generate an intense NMR signal at the low concentrations typical of biological levels. FIGS. 1(a)–(d) are fluorine-19 NMR spectra of the 1,1,1-trifluoro-2,2-bis(trifluoromethyl)-hexane PFTB in CDCl$_3$ in concentrations of 100 millimolar (FIG. 1(a)), 10 millimolar PFTB (FIG. 1(b)), 1 millimolar PFTB (FIG. 1(c)), and 0.1 millimolar PFTB (FIG. 1(d)) using a 10 millimolar (10 mM) CFCl$_3$ in CDCl$_3$ reference. The signal to noise ratio (S/N) was about 2 to 1 in FIG. 1(d), about 10 to 1 in FIG. 1(c), and about 100 to 1 in FIG. 1(b). Relative to the signal, the noise was not apparent due to the strength of the signal in FIG. 1(a).

EXAMPLE 2

Synthesis of Specific PFTB Fatty Acids for Metabolic Imaging of the Heart

In this example, a PFTB moiety-containing fatty acid was prepared which would be useful monitoring the metabolic activity of the heart. The particular material synthesized was 7,7,7-trifluoro-6,6-bis (trifluoromethyl)-heptanoic acid, i.e. —(CF$_3$)$_3$C—(CH$_2$)-CO$_2$H where n=4. This PFTB moiety-containing compound was prepared as follows. Using ethyl 5-bromovalerate as the alkylating agent, the standard PFTB reaction was run on a 50 mmole scale, analogous to the procedure given above. Crude product (PFTB fatty ester) was extracted from the reaction mixture, then 13.3 g yellow liquid were obtained by vacuum distillation. Without further purification, the sample was hydrolyzed by refluxing in 20% NaOH for about 3 hours. This second step yielded 6.6 g crude yellow solid, which was recrystallized from hot hexane. 4.0 g white crystalline solid (25%, free fatty acid, overall yield) were isolated, mp=75° C.

Another PFTB moiety-containing fatty acid was prepared and was used for monitoring the metabolic activity of a rabbit heart in Example 4, infra. The particular material synthesized was 8,8,8-trifluoro-7,7-bis(trifluoromethyl)octanoic acid (where n=5 in the above formula). This PFTB moiety-containing compound was prepared as follows. Using ethyl 6-bromohexanoate as the alkylating agent, the PFTB reaction was run on a 60 mmole scale, similar to the procedure given above. 17.4 g crude PFTB fatty ester were obtained, then hydrolyzed by refluxing in aqueous sodium hydroxide (20% NaOH) for about 3 hours. 10.0 g yellow liquid (free fatty acid) were isolated, but would not solidify. Vacuum distillation at 125° C./4torr gave 7.6 g (38% overall yield) clear, colorless fatty acid as a liquid.

EXAMPLE 3

Specific Synthesis of a Long Chain PFTB Fatty Acid

In this example, a PFTB moiety-containing long chain fatty acid was prepared which would also be useful for monitoring the metabolic activity of the heart. The particular material synthesized was 17,17,17-trifluoro-16,16-bis(trifluoromethyl)heptadecanoic acid. This PFTB moiety-containing compound was prepared as follows. Perfluoroisobutylene is condensed into a heterogeneous mixture of cesium fluoride in dry diglyme. Methyl 15-bromopentadecanoate, dissolved in diglyme, is then added dropwise. The reaction is quenched with water and the mixture extracted with ether to isolate the fluorinated ester product. The ester is readily hydrolyzed to the free fatty acid by refluxing in aqueous sodium hydroxide.

EXAMPLE 4

In-vivo Detection of PFTB Fatty Acid

In order to assess the detectability of the PFTB group in-vivo, PFTB labeled fatty acid 8,8,8-trifluoro-7,7-bis(-trifluoromethyl)octanoic acid from Example 2 was injected to result in a final circulating concentration comparable to naturally occurring levels. FIG. 2 presents the spectrum from a 4 cm. single turn coil placed on the chest, in the region of the heart, of a rabbit 0.25 hours after IV introduction of 10 ml of 24 mM (0.5 mM final circulating concentration) PFTB octanoic acid, dissolved in aqueous sodium bicarbonate (5% NaHCO$_3$). Data was acquired on a GECSI II with a horizontal bore of 40 cm, operating at 4.7 T. Spectra shown in FIG. 2 was generated from the FID with a spectral width of 5.0 kHz and a FID resolution of 1024. Five-hundred averages were acquired with a TR of 1 second. The resulting spectrum is a slightly broadened singlet with a signal to noise ratio of about 5:1.

EXAMPLE 5

Comparison of the Intensity of the PFTB Singlet with That of Other Fluorinated Samples Used in NMR/MRI In this example, the intensity of the PFTB singlet in a PFTB moiety-containing compound was compared to those of halothane, 5-fluororacil (5-FU), 3-fluoro-3-deoxy-D-glucose (3-FDG), perfluorotri-n-butylamine (FC-43), and perfluorodecalin. The (1,1,1-trifluoro-2,2-bis (trifluoromethyl)hexane of Example 1 was utilized as the PFTB moiety-containing compound herein.

The 10 mM solution of the PFTB moiety-containing compound (PFTB in Table 1) was prepared by dissolving 1.38 mg of this compound in 0.5 mL of CDCl$_3$.

The 100 mM halothane solution was prepared by dissolving 10 mg of halothane (2-bromo-2-chloro-1,1,1-trifluoroethane) in 0.5 mL of CDCl$_3$.

The 150 mM 5-FU solution was prepared by dissolving 10 mg of 5-FU in 0.5 mL of D$_2$O.

The 200 mM 3-FDG solution was prepared by dissolving 18 mg of 3-FDG in 0.5 ml of D$_2$O.

The FC-43 and perfluorodecalin samples were each 0.5 ml of the neat material; i.e., used as is without solvent.

Table 1 below compares the PFTB reporter group with five currently used fluorine imaging agents with respect to: the number of fluorine nuclei contributing to the signal, the number of separate resonance peaks (splitting), and the relative intensity of the signal, proportional to detectability at lower concentrations.

TABLE 1

Related Signal Intensities for Fluorinated Agents

| Agent | # Nuclei | Splitting Pattern | Intensity Relative to PFTB (%) |
|---|---|---|---|
| PFTB | 9 equiv. F's | singlet | 100% |
| Halothane | 3 equiv. F's | doublet | 17% |
| 5-FU | 1 fluorine | doublet | 6% |
| 3-FDG | 1 fluorine | doublet of triplets | 2% |
| FC-43 | 27 nonequiv. fluorines | multiple signals | 50% |
| Perfluorodecalin | 18 nonequiv. fluorines | multiple signals | 22% |

FIGS. 3–8 are the NMR spectra for the foregoing samples, respectively. These NMR spectra were obtained on an IBM NR/80 FT NMR Spectrometer, using 16K memory, run at 75.39 MHz for fluorine-19 NMR. The fluorine-19 chemical shifts were reported in ppm relative to $CFCl_3$ in FIGS. 3 and 4, relative to $CFCO_2H$ in FIGS. 5 and 6, relative to $CFCO_2CH_2CH_3$ in FIGS. 7 and 8.

The "Intensity Relative to PFTB (%)" in Table 1 was determined by first dividing the number of equivalent fluorine nuclei contributing to the most intense signal of the respective spectra by the splitting of the signal due to $J_{HF}$ or $J_{FF}$ coupling. This result was then dividing by the number of equivalent fluorine nuclei contributing to the most intense signal of the PFTB moiety-containing compound (i.e., 9), and then multiplying by 100. Table 2 contains the pertinent values for each of the agents in Table 1 corresponding to the spectra in FIGS. 3–8.

TABLE 2

| Agent | E.F.$^a$ | Splitting factor$^b$ | E.F./Splits |
|---|---|---|---|
| PFTB | 9 | 1 | 9 |
| Halothane | 3 | 2 | 1.5 |
| 5-FU | 1 | 2 | 0.5 |
| 3-FDG | 1 | 6 | 0.166 |
| FC-43 | 9 | 2 | 4.5 |
| Perfluorodecalin | 2 | 1 | 2 |

$^a$Number of equivalent fluorine nuclei contributing to most intense signal.
$^b$Factor for decreased signal intensity due to $J_{HF}$ or $J_{FF}$ coupling.

The foregoing clearly establishes the superiority of the PFTB moiety as a reporter group for fluorine-19 NMR which should carry over to fluorine-19 MRI as well.

EXAMPLE 6

(Prophetic) Fluorine - 19 Protoclos for Imaging Heart and Brain Metabolism - Fatty Acid Metabolism (Myocardial B-Oxidation)

PFTB labeled heptadecanoic acid, such as prepared in Example 2, would be dissolved in 5% aqueous sodium bicarbonate to a volume of 10 ml. Immediately following I.V. introduction of the fatty acid the patient would be placed in the magnetic resonance imager and R-wave synchronized $^1H$ images would be acquired of the heart in the axial, "long and short" axis orientation. Parameters would include 256 frequency and 128 phase encoding steps, TE=15 ms, TR=RR interval, 4 data averages, slice thickness=10 mm. Images at each ventricular level would be acquired at the end-diastolic and end-systolic phases of the cardiac cycle. These high spacial resolution images would later be combined with color coded $^{19}F$ fatty acid images to clearly match anatomy with metabolism. After calibration of the instrument for fluorine, short axis images at three levels of the heart would be acquired. Fluorine acquisition parameters would include a non-gated, 15 ms TE, 20 mm slice thickness, TR=2.5 sec., 64 phase and frequency steps and 8 data averages. Acquired fluorine images would be interpolated to a 256 images matrix, intensity distribution would be color coded and the $^1H$ and $^{19}F$ images combined. Comparison between mechanical function (end-diastolic vs. end-systolic) could then be compared to underlying metabolism. Applications would include: evaluation of patients with cardiomyopathy, evaluation of patients post myocardial infraction and evaluation of patients having had thrombolysis or angioplasty to open a obstructed coronary artery.

We have previously shown that the PFTB group can be easily incorporated into a varied group of biological substrates. Similar protocols have been designed for investigation of the glucose metabolism of the brain, the evaluation of labeled amino acids in the liver and tumor imaging utilizing PFTB labeled carcino-embryonic antigen (CEA).

In combination NMR imager/spectrometers which are available (usually limited to superconducting instruments above 2.0 T), one could make use of Hydrogen imaging, to provide precise anatomic detail and $^{19}F$ spectroscopy of regions selected from the $^1H$ image. See, J. Frahm et al., "Localized Proton NMR Spectroscopy in Different Regions of the Human Brain in Vivo. Relaxation Times and Concentrations of the Cerebral Metabolites," *Magnetic Resonance in Medicine*, vol. 11, pages 47–63 (1989). This would allow precise metabolic mapping, but require less administered fluorine than for fluorine imaging.

EXAMPLE 7

(Prophetic) $O_2$ Concentration Protocol

In order to display differences in regional $O_2$ (oxygen) concentration by means of the differences in fluorine-19 ($^{19}F$) T1 relaxation times, a canine model will be imaged with and without enhanced O2 ventilation after administration of 1,1,1,7,7,7,-hexafluoro-2,2,6,6-tetrakis (trifluoromethyl)heptane. This inert compound contains 18 equivalent fluorines and will allow distribution of the reporter group throughout perfused tissue.

Images will be acquired using a GE CS1 11 operating at a field strength of 4.7 T, with a horizontal bore of 40 cm allowing use of a standard canine preparation. Using a duel $^{19}F/^1H$ coil tuned for hydrogen, a series of 10 mm parallel coronal slices will be acquired with a TE of 12 ms and a TR of 200 ms with 4 averages and 128 phase and frequency encoding steps. After calibrating the imaging coil for $^{19}F$, baseline fluorine images will be acquired with a slice thickness of 30 mm, TE=12, 128 phase and frequency steps. Four image sets with TR's of 0.8, 1.2, 1.4 and 1.6 sec, respectively. Longitudinal relaxation times, obtained from various TR images, will be compared to those repeated as above but with the canine ventilated with pure O2 rather than room air. A single "T1" image will be constructed from the four various TR acquisitions. Comparison of intensity distribution will be made. The use of the PFTB group will allow lower fluorine concentrations and avoid routines normally required for analysis of nuclei displaying chemical shift artifacts.

We claim:

1. A composition for use in NMR imaging and spectroscopy, said composition comprising:
   a derivatized biological compound, wherein said derivatized biological compound is a biologically active host molecule derivatized so as to contain at least one perfluoro-t-butyl moiety, and
   a carrier for said derivatized biological compound, wherein said host molecule is selected from the group consisting of fatty acids and amino acids.

2. A method of NMR imaging or spectroscopy comprising administering to a subject a composition comprising a derivatized host compound and a carrier for said derivatized host compound, wherein said derivatized host compound is a host compound derivatized so as to contain at least one perfluoro-t-butyl moiety, each of said at least one perfluoro-t-butyl moiety having nine (9) magnetically equivalent fluorine nuclei which generate a single, intense resonance for easy detection in said imaging or spectroscopy, wherein said host compound is selected from the group consisting of fatty acids and amino acids.

* * * * *